(12) United States Patent
Gibson et al.

(10) Patent No.: US 6,333,292 B1
(45) Date of Patent: Dec. 25, 2001

(54) CATALYSTS FOR OLEFIN POLYMERIZATION

(75) Inventors: Vernon Charles Gibson, London; Brian Stephen Kimberley, Sunbury-on-Thames, both of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/301,074

(22) Filed: Apr. 28, 1999

(30) Foreign Application Priority Data

Apr. 29, 1998 (GB) ................................................ 9809207

(51) Int. Cl.$^7$ ................................................ B01J 31/18
(52) U.S. Cl. ........................ 502/167; 502/123; 502/125; 502/102; 502/156; 502/172; 526/141; 526/142; 526/147; 526/161; 526/164; 556/50; 556/51; 556/449
(58) Field of Search ..................... 502/123, 125, 502/102, 156, 167, 172; 556/50, 51, 449; 526/141, 142, 147, 161, 164

(56) References Cited

U.S. PATENT DOCUMENTS

| 5,541,270 A | 7/1996 | Chinh et al. ................... 526/68 |
| 5,637,660 A | * 6/1997 | Nagy et al. .................. 526/160 |
| 5,714,556 A | * 2/1998 | Johnson et al. ............. 526/135 |

FOREIGN PATENT DOCUMENTS

| EP | 0 874 005 | 10/1998 |
| EP | 0 950 667 | * 10/1999 |
| JP | 11-80228 | 3/1999 |
| JP | 11158189 | * 6/1999 |
| JP | 11199592 | * 7/1999 |
| WO | 95/26355 | 10/1995 |
| WO | WO95/26355 | * 10/1995 |

OTHER PUBLICATIONS

Coleman, Applied Catalysis, 22, 345–359, 1986.*

* cited by examiner

*Primary Examiner*—David W. Wu
*Assistant Examiner*—Ling-Siu Choi
(74) *Attorney, Agent, or Firm*—Finnegan, Henderson, Farabow, Garrett and Dunner, L.L.P.

(57) ABSTRACT

Novel compounds are disclosed comprising the skeletal unit depicted in Formula (I)

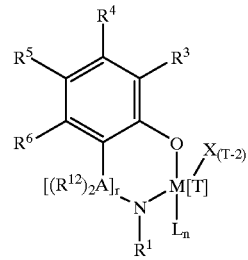

Formula (I)

wherein O is oxygen; N is nitrogen; $R^1$ is hydrogen, hydrocarbyl, substituted hydrocarbyl, heterohydrocarbyl or substituted heterohydrocarbyl; $R^3$, $R^4$, $R^5$ and $R^6$ are hydrogen or hydrocarbyl or heterohydrocarbyl groups containing 1 to 10 carbon atoms and the $R^{12}$ groups are independently selected from hydrogen, hydrocarbyl, substituted hydrocarbyl, heterocarbyl and substituted heterocarbyl; A is carbon or silicon; and r is 1 or more; M is scandium, yttrium, or a Group IV or Group V metal or a lanthanide or actinide; T is the oxidation state of M and is II or greater; X represents a monodentate atom or group covalently or ionically bonded to M; L is a mono- or bidentate molecule datively bound to M, and n is from 0 to 5.

12 Claims, No Drawings

CATALYSTS FOR OLEFIN POLYMERIZATION

The present invention relates to novel transition metal compounds and to their use as polymerisation catalysts.

The use of certain transition metal compounds to polymerise 1-olefins, for example, ethylene, is well established in the prior art. The use of Ziegler-Natta catalysts, for example, those catalysts produced by activating titanium halides with organometallic compounds such as triethylaluminiur, is fundamental to many commercial processes for manufacturing polyolefins. Over the last twenty or thirty years, advances in the technology have lead to the development of Ziegler-Natta catalysts which have such high activities that that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

Commodity polyethylenes are commercially produced in a variety of different types and grades. Homopolymerisation of ethylene with transition metal based catalysts leads to the production of so-called "high density" grades of polyethylene. These polymers have relatively high stiffness and are usefull for making articles where inherent rigidity is required. Copolymerisation of ethylene with higher 1-olefins (eg butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so called "low density" polyethylene produced by the high pressure free radical catalysed polymerisation of ethylene. Such polymers and copolymers are used extensively in the manufacture of flexible blown film.

An important feature of the microstructure of the copolymers of ethylene and higher 1-olefins is the manner in which polymerised comonomer units are distributed along the "backbone" chain of polymerised ethylene units. The conventional Ziegler-Natta catalysts have tended to produce copolymers wherein the polymerised comonomer units are clumped together along the chain. To achieve especially desirable film properties from such copolymers the comonomer units in each copolymer molecule are preferably not clumped together, but are well spaced along the length of each linear polyethylene chain. In recent years the use of certain metallocene catalysts (for example biscyclopentadienylzirconiumdichloride activated with alumoxane) has provided catalysts with potentially high activity and capable of providing an improved distribution of the comonomer units. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

An object of the present invention is to provide a novel catalyst suitable for polymerising olefins, and especially for polymerising ethylene alone or for copolymerising ethylene with higher 1-olefins. A further object of the invention is to provide an improved process for the polymerisation of olefins, especially of ethylene and $C_{2-20}$ linear or branched α-olefins, or the copolymerisation of ethylene with higher 1-olefins to provide homopolymers and copolymers having controllable molecular weights. For example, using the catalyst of the present invention there can be made a wide variety of polyolefins such as, for example, liquid polyolefins, resinous or tacky polyolefins, solid polyolefins suitable for making flexible film and solid polyolefins having high stiffness.

In its broadest aspect the present invention provides a nitrogen-containing transition metal complex compound comprising the skeletal unit depicted in Formula (I)

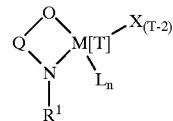

Formula (I)

Formula (I)
wherein O is oxygen, N is nitrogen, Q represents a divalent organic group or a group based on a Group 14 atom; $R^1$ is hydrogen, hydrocarbyl, substituted hydrocarbyl, heterohydrocarbyl or substituted heterohydrocarbyl; M is scandium yttrium, or a Group IV or Group V metal or a lanthanide or actinide; T is the oxidation state of M and is II or greater; X represents a monodentate atom or group covalently or ionically bonded to M; L is a mono- or bidentate molecule datively bound to M, and n is from 0 to 5. Q may be datively coordinated to the metal M.

Preferred metals are those of Group IV, or scandium or yttrium. More preferred are Ti(IV), Ti(III), Ti(II), Zr(IV), Zr(III), Zr(II), Hf(IV), Hf(III), Hf(II), Sc(III) and Y(III).

L is preferably an ether, alcohol, amine, ester, phosphine, alkene, alkyne or arene, and in particular may be a diene.

In a preferred embodiment, the present invention provides a compound comprising the skeletal unit depicted in Formula A:

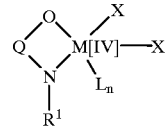

Formula A

Formula A wherein O is oxygen, N is nitrogen, Q represents a divalent organic group or a group based on a Group 14 atom, M is titanium(IV), zirconium(IV) or hafnium (IV), $R^1$ is hydrogen, hydrocarbyl, substituted hydrocarbyl, heterohydrocarbyl or substituted heterohydrocarbyl, and each X represents a monodentate atom or group covalently or ionically bonded to M. It is preferred that n is zero.

The divalent bridging group Q can be, for example, the simple divalent group $CR_2$ or a polyalkylene chain $(CR_2)_q$, a silane bridge $(SiR_2)_m$, or a polyalkylene-silane bridge $(CR_2)_p(SiR_2)_m$, wherein the R groups can be, for example, independently selected from hydrogen, hydrocarbyl, substituted hydrocarbyl, heterocarbyl and substituted heterocarbyl, m is one or more, p is one or more and q is two or more. Two or more of the R groups may connect together, for example, to form a carbocyclic or heterocyclic ring system within the bridging group Q. Specific examples of Q include methylene, dimethylmethylene, ethylene, propylene, dimethylpropylene, 1,1-dimethyl-3,3-dimethylpropylene or butylene; dimethylsilyl, methylphenylsilyl, tetramethyldisiloxane, 1,1,4,4-tetramethyldisilylethylene and dimethylgermanyl; or Q may be phenyl.

In the complex compound depicted in Formula A of the present invention the bridging group Q preferably comprises a saturated or unsaturated ring system, for example, a benzene, cyclohexene, cyclohexane, pyrazole, pyridine, piperidine, pyrazine, pyrimidine, or a thiazole ring system, or a polynuclear homocyclic or heterocyclic system such as, for example, naphthalene, quinoline or imidazole. For example, such a ring system may be a substituent on the divalent bridging group, or may be the bridging group itself or a part thereof. Thus for example, Q may comprise a benzene ring system. Such a benzene ring system may be present, for example, as a direct ortho-phenylene bridge between the oxygen and nitrogen atoms in formula A, or as an ortho-phenylene group in series with another atom or atoms in the bridge, or as a phenyl substituent to another atom in the bridge.

A particularly preferred compound in accordance with the present invention comprises a skeletal unit having the formula (Formula B):

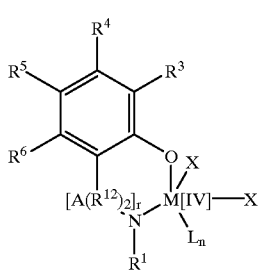

Formula B wherein $R^1$, M, X, L and n are as defined above, $R^3$, $R^4$, $R^5$ and $R^6$ are preferably hydrogen or hydrocarbyl or heterohydrocarbyl groups containing 1 to 10 carbon atoms and the $R^{12}$ groups are independently selected from hydrogen, hydrocarbyl, substituted hydrocarbyl, heterocarbyl and substituted heterocarbyl; A is carbon or silicon; r is 1 or more, for example 1 to 5. Examples of the $R^3$, $R^4$, $R^5$ and $R^6$ groups are hydrogen, methyl, ethyl, n-propyl, n-butyl, n-hexyl, and n-octyl. Examples of the $R^{12}$ groups are hydrogen, methyl, ethyl, n-propyl, n-butyl, n-hexyl, n-octyl, methoxy, ethoxy, dimethylamino, phenyl and naphthyl. Preferably A is carbon, and n is zero.

In the complexes above, $R^1$ is preferably alkyl or aryl, for example, methyl, ethyl, propyl, n-butyl, tertiary-butyl, phenyl, 1-naphthyl, 2-naphthyl, 2-ethylphenyl, 2,6-diisopropylphenyl, 2,6-di-n-butylphenyl, 2,6-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro-2,6-diethylphenyl, 2,6,bis(2,6-dimethylphenyl)phenyl, adamantyl, triphenylmethyl, 2,6-dimethyl-4-t-butylphenyl, 2,4,6-triphenylphenyl, 2,3,4,5,6-pentamethylphenyl, and 2-methylenepyridine.

The univalent radical X in the complex of Formula A and Formula B is preferably selected from $C_1$–$C_{10}$ alkyl, $C_6$–$C_{10}$ aryl, halide, hydride, hydrocarbyloxide, and amide. Examples of such groups are N,N-dimethylamido, N,N-diethylamido, chloro, bromo, methyl, ethyl, n-propyl, isopropyl, benzyl, n-butyl and n-octyl.

In preferred complexes of Formula B, $[A(R^{12})_2]_r$ is $CH_2$, each X is $NMe_2$, $R^4$ and $R^6$ are H, $R^3$ and $R^5$ are H or t-Bu, and $R^1$ is t-Bu, 2,6-dimethylphenyl, naphthyl, phenyl or adamantyl.

Particularly preferred novel compounds of Formula A of the present invention are the compounds comprising the skeletal unit as depicted in Formula C:

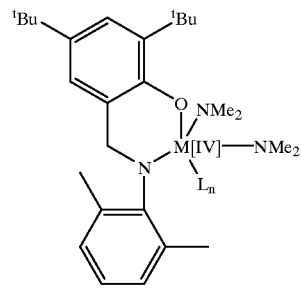

Formula C

In the formula above, n may be zero.

In the solid state, the compound of Formula C exists as a dimer as in Formula D:

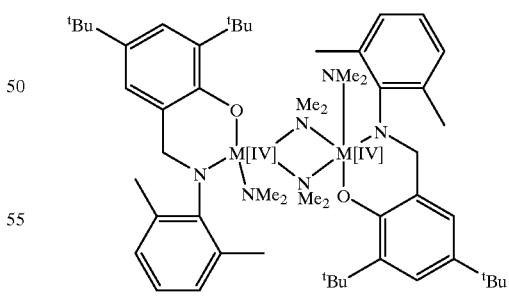

The present invention further provides a catalyst for the polymerisation of 1-olefins comprising (1) the compound of Formula (I) above, and optionally (2) an activator. Preferred catalysts contain compounds of the Formulae A, B, C or D above.

The activator for the catalyst of the present invention is suitably selected from organoaluminium compounds and hydrocarbylboron compounds. Suitable organoaluminium compounds include compounds of the formula $AlR_3$, where each R is independently $C_1$–$C_{12}$ alkyl or halo. Examples include trimethylalurninium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups. Alkylalumoxanes such as methylalumoxane (MAO) are preferred.

Mixtures of alkylalumoxanes and trialkylaluminium compounds are particularly preferred, such as MAO with TMA or TIBA. In this context it should be noted that the term "alkylalumoxane" as used in this specification includes alkylalumoxanes available commercially which may contain a proportion, typically about 10 wt %, but optionally up to 50 wt %, of the corresponding trialkyaluminium; for instance, commercial MAO usually contains approximately 10 wt % trimethylaluminium (TMA), whilst commercial MMAO contains both TMA and TIBA. Quantities of alkylalumoxane quoted herein include such trialkylaluminium impurities, and accordingly quantities of trialkylaluminium compounds quoted herein are considered to comprise compounds of the formula $AlR_3$ additional to any $AlR_3$ compound incorporated within the alkylalumoxane when present.

Examples of suitable hydrocarbylboron compounds are boroxines, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl) boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per metal atom M, particularly when it is desired to use an alumoxane activator.

A further aspect of the present invention provides a polymerisation catalyst system comprising (1) the compound of the invention as defined above, (2) an activating quantity of at least one activator compound preferably selected from organoaluminium and hydrocarbylboroncompounds, and (3) a neutral Lewis base.

Neutral Lewis bases are well known in the art of Ziegler-Natta catalyst polymerisation technology. Examples of classes of neutral Lewis bases suitably employed in the present invention are unsaturated hydrocarbons, for example, alkenes (other than 1-olefins) or alkynes, primary, secondary and tertiary amines, amides, phosphoramides, phosphines, phosphites, ethers, thioethers, nitriles, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (3) of the catalyst system can be brought together simultaneously or in any desired order. However, if components (2) and (3) are compounds which interact together strongly, for example, form a stable compound together, it is preferred to bring together either components (1) and (2) or components (1) and (3) in an initial step before introducing the final defined component. Preferably components (1) and (3) are contacted together before component (2) is introduced. The quantities of components (1) and (2) employed in the preparation of this catalyst system are suitably as described above in relation to the catalysts of the present invention. The quantity of the neutral Lewis Base [component (3)] is preferably such as to provide a ratio of component (1):component (3) in the range 100:1 to 1:1000, most preferably in the range 1:1 to 1:20. Components (1), (2) and (3) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating, to higher temperatures e.g. up to 120° C. can be carried out if desired, e.g. to achieve better mixing of the components. It is preferred to carry out the bringing together of components (1), (2) and (3) in an inert atmosphere.(e.g. dry nitrogen) or in vacuo. If it is desired to use the catalyst on a support material (see below), this can be achieved, for example, by preforming the catalyst system comprising components (1), (2) and (3) and impregnating the support material preferably with a solution thereof, or by introducing to the support material one or more of the components simultaneously or sequentially. If desired the support material itself can have the properties of a neutral Lewis base and can be employed as, or in place of, component (3). An example of a support material having neutral Lewis base properties is poly(aminostyrene) or a copolymer of styrene and aminostyrene (ie vinylaniline).

The catalysts of the present invention can if desired comprise more than one of the defined compounds. Alternatively, the catalysts of the present invention can also include one or more other types of transition metal compounds or catalysts, for example, nitrogen containing Fe or Co catalysts such as those described in our copending, applications PCT/GB98/02638. Examples of such other catalysts include 2,6-diacetylpyridinebis(2,4,6-trimethyl anil)$FeCl_2$.

The catalysts of the present invention can also include one or more other transition metal compounds, such as those of the type used in conventional Ziegler-Natta catalyst systems, metallocene-based catalysts, monocyclopentadienyl- or constrained geometry based catalysts, or heat activated supported chromium oxide catalysts (eg Phillips-type catalyst).

The catalysts of the present invention can be unsupported or supported on a support material, for example, silica, alumina, $MgCl_2$ or zirconia, or on a polymer or prepolymer, for example polyethylene, polypropylene, polystyrene, or poly(aminostyrene).

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the compound of the invention.

The present invention further provides a process for the polymerisation and copolymerisation of 1-olefins, comprising contacting the monomeric olefin under polymerisation conditions with the polymerisation catalyst of the present invention.

The polymerisation conditions can be, for example, solution phase, slurry phase or gas phase, with polymerisation temperatures ranging from –100° C. to +300° C. If desired, the catalyst can be used to polymerise ethylene under high pressure/high temperature process conditions wherein the polymeric material forms as a melt in supercritical ethylene. Preferably the polymerisation is conducted under gas phase fluidised bed or stirred bed conditions.

Slurry phase polymerisation conditions or gas phase polymerisation conditions are particularly useful for the production of high or low density grades of polyethylene, and polypropylene. In these processes the polymerisation conditions can be batch, continuous or semi-continuous. In the slurry phase process and the gas phase process, the catalyst is generally fed to the polymerisation zone in the form of a particulate solid. This solid can be, for example, an undiluted solid catalyst system formed from the complex of the invention and an activator, or can be the solid complex alone. In the latter situation, the activator can be fed to the polymerisation zone, for example as a solution, separately from or together with the solid complex. Preferably the catalyst system or the transition metal complex component of the catalyst system employed in the slurry polymerisation and gas phase polymerisation is supported on a support material. Most preferably the catalyst system is supported on a support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques.

In the slurry phase polymerisation process the solid particles of catalyst, or supported catalyst, are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor, e.g. of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature rang,es can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of nitrogen-containing transition metal complex employed in the catalyst system). This means that relatively very small quantities of transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (e.g. as occurs in most commercial slurry and gas phase polymerisation processes), the amount of transition metal complex in the produced polymer can be very small.

Suitable monomers for use in the polymerisation process of the present invention are, for example, ethylene and $C_{2-20}$ α-olefins, specifically propylene, 1-butene, 1-pentene, 1-hexene, 1-heptene, 1-octene, 1-nonene, 1-decene, 1-undecene, 1-dodeene, 1-tridecene, 1-tetradecene, 1-pentadecene, 1-hexadecene, 1-heptadecene, 1-octadecene, 1-nonadecene, and 1-eicosene. Other monomers include methyl methacrylate, methyl acrylate, butyl acrylate, acrylonitrile, vinyl acetate, and styrene. Preferred monomers for homopolymerisation processes are ethylene and propylene. The catalyst can also be used for copolymerising ethylene with other 1-olefins such as propylene, 1-butene, 1-hexene, 4-methylpentene-1, and octene.

The catalyst of the present invention can also be used for copolymerising ethylene with other monomeric materials, for example, methyl methacrylate, methyl acrylate, butyl acrylate, acrylonitrile, vinyl acetate, and styrene.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymnerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

Methods for operating gas phase fluidised bed processes for making polyethylene and ethylene copolymers are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and sprayed back into the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

In use, polymers or copolymers made by the process of the invention in the form of a powder are conventionally compounded into pellets. Additionally or alternatively, additives may be incorporated, such as antioxidants or neutralisers. The polymers may be blown into films, or may be used for making a variety of moulded or extruded articles such as pipes, and containers such as bottles or drums.

The present invention further provides a process for the polymerisation and copolymerisation of 1-olefins comprising contacting the monomeric olefin under polymerisation conditions with the catalyst of the present invention. The polymerisation conditions can be, for example, solution phase, slurry phase or gas phase. If desired, the catalyst can be used to polymerise ethylene under high pressure/high temperature process conditions wherein the polymeric material forms as a melt in supercritical ethylene. Preferably the polymerisation is conducted under gas phase fluidised bed conditions. Suitable monomers for use in the polymerisation process of the present invention are, for example, ethylene, propylene, butene, hexene, methyl methacrylate, methyl acrylate, butyl acrylate, acrylonitrile, vinyl acetate, and styrene. Preferred monomers for homopolymerisation processes are ethylene and propylene. The catalyst is especially useful for copolymerising ethylene with other 1-olefins such as propylene, 1-butene, 1-hexene, 4-methylpentene-1, and octene. Methods for operating the gas phase fluidised bed process for making polyethylene and ethylene copolymers are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (eg nitrogen) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out and can be separated and sprayed into the bed, or recycled to the bed with the recycle gas. It is preferred to reintroduce the condensed liquid into the bed using the process described in our U.S. Pat. No. 5541270.

In use, polymers or copolymers made by the process of the invention in the form of a powder are conventionally compounded into pellets. Additionally or alternatively, additives may be incorporated, such as antioxidants or neutralisers. The polymers may be blown into films, or may be used for making a variety of moulded or extruded articles such as pipes, and containers such as bottles or drums.

The present invention is illustrated in the following Examples.

EXAMPLES

Example 1 shows the preparation of a novel zirconium complex in accordance with the present invention. Examples 2 and 3 illustrate the use of this novel zirconium complex as a catalyst in the polymerisation of ethylene.

In the Examples all manipulations of air/moisture-sensitive materials were performed on a conventional vacuum/inert atmosphere (nitrogen) line using standard Schlenk line techniques, or in an inert atmosphere glove box.

Example 1

1.1—Preparation of Intermediate 1

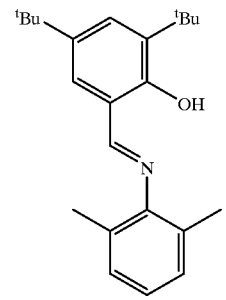

Intermediate 1

Intermediate 1

To a stirred solution of 3,5-di-tert-butyl-2-hydroxybenzaldehyde (4.97 g, 21.2 mmol) in methanol (100 ml) was added 2,6-dimethylaniline (2.6 ml, 21.2 mmol) and formic acid (0.5 ml). After 60 minutes of stirring the solution was dried over sodium sulphate. Filtration of the reaction solution and removal of the volatile components under reduced pressure yielded a yellow oil. Repeated washing of the oil with pentane (5×5 ml) at −78° C. afforded a yellow solid (Intermediate 1). Yield 4.8 g, 67%.

The reagents 3,5-di-tert-butyl-2-hydroxybenzaldehyde and 2,6-dimethylaniline were supplied by Aldrich.

1.2—Preparation of Intermediate 2

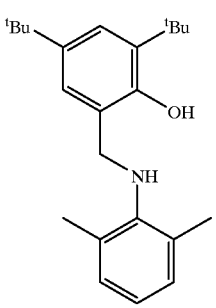

Intermediate 2

Intermediate 2

To a stirred suspension of LiAlH$_4$ (1.12 g, 29.5 mmol) in Et$_2$O (100 ml) at 0° C. was added dropwise a solution of Intermediate 1 (3.30 g, 9.84 mmol) in Et$_2$O (20 ml). The suspension was warmed to room temperature and stirred for 30 minutes. Slow addition of water (1.5 ml) to the reaction mixture was followed by filtration. The reaction solution was dried over sodium sulphate, filtered and the volatile components were removed under reduced pressure to give a beige solid (Intermediate 2). Yield 3.3 g, 98%.

1.3—Preparation of a Zirconium Complex

A compound having the structure below

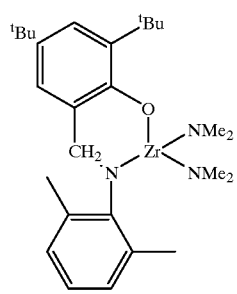

was prepared as follows. Intermediate 2 (0.89 g, 2.6 mmol) in toluene was added to a stirred solution of Zr(NMe$_2$)$_4$ (0.70 g, 2.6 mmol) in toluene (50 ml). The reaction mixture was stirred for 14 hours at 90° C. under a positive pressure of nitrogen. Removal of the volatile components of the reaction gave a yellow solid zirconium complex. Recrystallisation from toluene (−20° C.) afforded yellow rhombic crystals. Yield 1.03 g, 77%. The Zr(NMe$_2$)$_4$ was prepared by the method described by G. Chandra, M. F. Lappert in *J. Chem. Soc(A)*. 1968. 1940–1945.

The zirconium complex prepared as described in Example 1 exists in the solid state as the dimer:

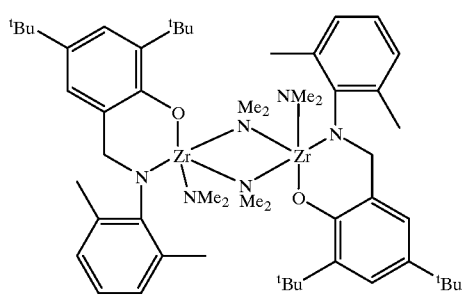

Polymerisation Tests

The polymerisation tests described in Examples 2 and 3 below were carried out using the following procedure. A 1 liter autoclave was pressure tested with 10 bar of N$_2$ for 10 minutes. The autoclave was then dried by raising the temperature of the surrounding water jacket to 85° C. and purging with a flow of nitrogen (2 liter per minute) for 1 hour. The temperature of the water jacket was then set to 50° C. and the system allowed to equilibrate. Scavenger and 500 ml of iso-butane was then introduced into the autoclave via the liquid injection system. This was stirred until the pressure and temperature were steady. The catalyst was pre-weighed into a Schlenk tube in a glove box and was prepared for injection into the polymerisation system. The autoclave was then pressurised with 10 bar of ethylene and allowed to reach equilibrium state. The catalyst solution was passed via a syringe into the injection system, the data collection system was activated and then the catalyst solution was injected into the system using N$_2$ overpressure. The pressure increase in the system was then compensated for by adjustment of the ethylene mass flow controller. After the desired time period the polymerisation was terminated by closing the ethylene supply and venting the autoclave to the atmosphere.

The polymer formed was scraped from the walls of the autoclave and washed with MeOH acidified with dilute Hcl, and then with aqueous MeOH before being dried under vacuum.

Example 2

A solution of trimethylaluminium (TMA) in hexane fraction (2 ml, 4×10$^{-3}$ mols) was added to the reactor as scavenger. The solid zirconium complex prepared in Example 1 (25 mg, 4.99×10$^{-5}$ mols), prealkylated with TMA (0.24 ml, 4.89×10$^{-4}$ mols of a 2 molar solution in n-hexanes) and methylalumoxane (MAO) (13 cl, 3.66×10$^{-4}$ mols of a 1.5M solution in toluene) was added to the reaction in a single injection. The ratio of catalyst:pre-alkylator:co-catalyst ratio was 1:10:400. The reaction vessel was set to be maintained at 50° C. throughout the run, which lasted 35 minutes. The yield of polymer isolated was 44.0 g, corresponding to an activity of 154.3 g mmol$^{-1}$hr$^{-1}$bar$^{-1}$.

Example 3

A solution of TMA in hexane fraction (2 ml, 4×10$^{-3}$ mols) was added to the reactor as scavenger. The solid zirconium complex prepared in Example 1 (2.5 mg; 4.89×10$^{-6}$ mols), prealkylated with TMA (0.02 ml, 4.89×10$^{-5}$ mols of a 2 molar solution in n-hexanes) and MAO (1.3 ml, 3.66×10$^{-3}$ mols of a 1.5M solution in toluene) was added to the reactior in a single injection. The ratio of catalyst:co-catalyst:pre-alkylator ratio was 1:400:10. The reaction vessel was maintained at 50° C. throughout the run, which lasted 60 minutes. The isolated yield of polymer was 8.3 g, corresponding to an activity of 170 g mmol$^{-1}$bar$^{-1}$hr$^{-1}$.

Example 4

4.1—Preparation of Intermediate 3

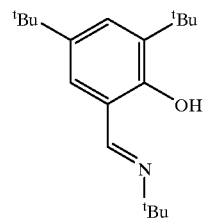

Intermediate 3

Intermediate 3

To a stirred solution of 3,5-di-tert-butyl-2-hydroxybenzaldehyde (5.11 g, 21.8 mmol) in methanol (30 ml) was added tert-butylamine (2.29 g, 21.8 mmol) and formic acid (0.5 ml). The reaction mixture was stirred for 12 hours during which time a yellow precipitate formed. Filtration of the supernatent solution afforded Intermediate 3 as a yellow solid. Yield 3.8 g, 60%.

The reagent tert-butylamine was supplied by Aldrich.

4.2—Preparation of Intermediate 4

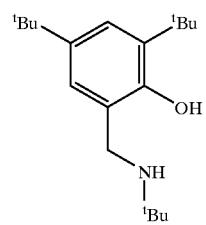

Intermediate 4

Intermediate 4

To a stirred suspension of LiAlH$_4$ (1.18 g, 31.1 mmol) in Et$_2$O (100 ml) at 0° C. was added dropwise a solution of Intermediate 3 (3.00 g, 10.36 mmol) in Et$_2$O (20 ml). The suspension was warmed to room temperature and stirred for 30 minutes. Slow addition of water (1.5 ml) to the reaction mixture was followed by filtration. The reaction solution was dried over sodium sulphate, filtered and the volatile components were removed under reduced pressure to give a beige solid (Intermediate 4). Yield 2.97 g, 98%.

4.3—Preparation of a Zirconium Complex

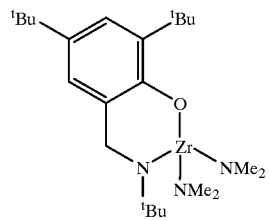

The compound having the above structure was prepared as follows. Intermediate 4 (1.11 g, 3.8 mmol) in toluene was added to a stirred solution of Zr(NMe$_2$)$_4$ (1.03 g, 3.85 mmol) in toluene (50 ml). The reaction mixture was stirred for 14 hours at 90° C. under a positive pressure of nitrogen. Removal of the volatile components of the reaction gave a yellow solid zirconium complex. Recrystallisation from toluene (−20° C.) afforded yellow rhombic crystals of the above compound. Yield 1.43 g, 80%.

Example 5

5.1—Preparation of Intermediate 5

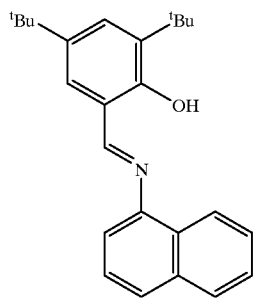

Intermediate 5

To a stirred solution of 3,5-di-tert-butyl-2-hydroxybenzaldehyde (5.07 g, 21.5 mmol) in methanol (30 ml) was added naphthylamine (3.08 g, 21.5 mmol) and formic acid (0.5 ml). The reaction mixture was stirred for 12 hours during which time a yellow precipitate formed. Filtration of the supernatent solution and washing with pentane (3×50 mls) afforded Intermediate 5 as a yellow solid. Yield 5.6 g, 72%.

The reagent naphthylamine was supplied by Aldrich.

5.2—Preparation of Intermediate 6

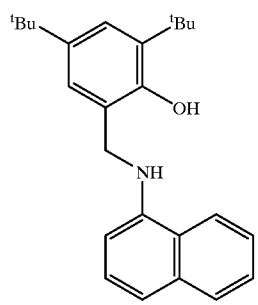

Intermediate 6

Intermediate 6
To a stirred suspension of LiAlH$_4$ (1.11 g, 29.3 mmol) in Et$_2$O (100 ml) at 0° C. was added dropwise a solution of Intermediate 5 (3.50 g, 9.74 mmol) in Et$_2$O (20 ml). The suspension was warmed to room temperature and stirred for 30 minutes. Slow addition of water ( 1.5 ml) to the reaction mixture was followed by filtration. The reaction solution was dried over sodium sulphate, filtered and the volatile components were removed under reduced pressure to give a beige solid (Intermediate 4). Yield 3.21 g, 91%.

5.3—Preparation of a Zirconium Complex (Complex 3)

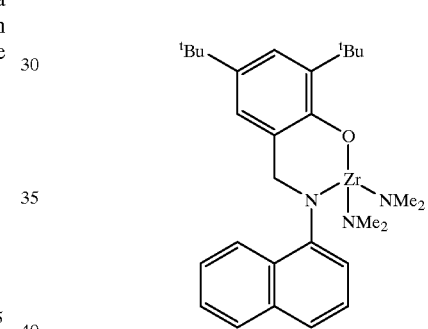

Complex 3

A compound having the above structure was prepared as follows. Intermediate 6 (0.99 g, 2.7 mmol) in toluene (20 ml) was added to a stirred solution of Zr(NMe$_2$)$_4$ (0.73 g, 2.73 mmol) in toluene (50 ml). The reaction mixture was stirred for 48 hours at 90° C. under a positive pressure of nitrogen. Removal of the volatile components of the reaction gave an orange solid. Recrystallisation from toluene at ambient temperature afforded orange crystals of the above compound. Yield 0.92 g, 63%.

Polymerisation Tests

The polymerisation tests described in the Examples below were were carried out using the following procedure. A 1 liter autoclave was pressure tested with 10 bar of N$_2$ for 10 minutes. The autoclave was then dried by raising the temperature of the surrounding water jacket to 85° C. and purging with a flow of nitrogen (2 liter per minute) for 1 hour. The temperature of the water jacket was then set to 50° C. and the system allowed to equilibrate. Scavenger and 500 ml of iso-butane was then introduced into the autoclave via the liquid injection system. This was stirred until the pressure and temperature were steady. The catalyst was pre-weighed into a Schlenk tube in a glove box and was prepared for injection into the polymerisation system. The autoclave was then pressurised with 10 bar of ethylene and allowed to reach equilibrium state. The catalyst solution was passed via a syringe into the injection system, the data collection system was activated and then the catalyst solution was injected into the system using $N_2$ overpressure. The pressure increase in the system was then compensated for by adjustment of the ethylene mass flow controller. After the desired time period the polymerisation was terminated by closing the ethylene supply and venting the autoclave to the atmosphere.

The polymer formed was scraped from the walls of the autoclave and washed with MeOH acidified with dilute HCl, and then with aqueous MeOH before being dried under vacuum.

Example 6

A solution of trimethylaluminium (TMA) in hexane fraction (2 ml, $4 \times 10^{-3}$ mols) was added to the reactor as scavenger. The solid zirconium complex prepared in Example 4.3 above (25 mg, $4.89 \times 10^{-5}$ mols), prealkylated with TMA (0.24 ml, $4.89 \times 10^{-4}$ mols of a 2 molar solution in n-hexanes) and methylalumoxane (MAO) (13 cl, $3.66 \times 10^{-4}$ mols of a 1.5M solution in toluene) was added to the reaction in a single injection. The ratio of catalyst:prealkylator:co-catalyst ratio was 1:10:400. The reaction vessel was set to be maintained at 50° C. throughout the test. An exotherm (1° C.) and gradually rising ethylene flow was recorded. The ethylene flow remained at 60% flow for 20 minutes until a gentle drop in ethylene flow was observed (35%) and remained until termination of the run (35 minutes). The yield of polymer isolated was 44.0 g, corresponding to an activity of 154.3 g/mmol.hr.bar.

Example 7

A solution of trimethylaluminium (TMA) in hexane fraction (2 ml, $4 \times 10^{-1}$ mols) was added to the reactor as scavenger. The solid zirconium complex prepared in Example 4.3 above (25 mg, $5.33 \times 10^{-5}$ mols), prealkylated with TMA (0.27 ml, $5.33 \times 10^{-4}$ mols of a 2 molar solution in n-hexanes) and methylalumoxane (MAO) (27 ml, $4.00 \times 10^{-2}$ mols of a 1.5M solution in toluene) was added to the reaction in a single injection. The ratio of catalyst:prealkylator:co-catalyst ratio was 1:10:750. The reaction vessel was set to be maintained at 50° C. throughout the test. The yield of polymer isolated was 18.5 g, corresponding to an activity of 35 g/mmol.hr.bar.

Example 8

Supported Catalyst

A solution of triisobutylylaluminium (TiBAl) in hexane fraction (2 ml, $2 \times 10^{-3}$ mols) and trimethylaluminium (TMA) in hexane fraction (2 ml, $4 \times 10^{-3}$ mols) were added to the reactor as scavengers. The solid zirconium complex prepared in Example 5.3 above (15 mg, $2.78 \times 10^{-5}$ mols), prealkylated with TMA (0.5 ml, $2.5 \times 10^{-4}$ mols of a 2 molar solution in n-hexanes) and methylalumoxane (MAO) (1 ml, $6.7 \times 10^{-4}$ mols of a 1.5M solution in toluene) was added to a slurry of ES70x (0.4 g, calcined in a nitrogen purge stream for 14 hours at 500° C.) in toluene (10 mls). The reaction mixture was heated at 80° C. for 15 minutes then added to the reactor in a single injection. The reaction vessel was set to be maintained at 75° C. and 18 bar ethylene throughout the 155 minute test. The yield of polymer isolated was 22.6 g, corresponding to an activity of 15 g/mmol.hr.bar.

Example 9

9.1—Synthesis of 3,5-di-tertbutyl salicylaldehyde N-2,4,6-trimethylphenyl imine (Intermediate 7)

3,5-di-tert-butyl-2-hydroxy benzaldehyde and 2,4,6-trimethyl aniline were purchased from Aldrich and used without further purification. A 500 mL flask equipped with a reflux condenser was loaded with 25 g (0.106 mol) 3,5-di-tertbutylsalicylaldehyde, 15.0 mL (0.106 mol) 2,4,6-trimethylaniline and 250 mL EtOH. The mixture was refluxed for 12 h and then allowed to stand in air for 12 h. The yellow crystals thus evolved were collected via filtration to give 36.5 g (97%) of Intermediate 7.

9.2—Synthesis of 3,5-di-tertbutyl salicyl-N-2,4,6-trimethyl phenyl amine (Intermediate 8)

In an $N_2$ glovebox, a 250 mL schlenk was loaded with 8.3 g (217 mmol) lithium aluminium hydride and covered with 100 mL diethyl ether. At 0° C., 25.5 g (72.5 mmol) 3,5-di-tertbutyl salicylaldehyde N-2,4,6-trimethylphenyl imine was added to the slurry in 100 mg batches over 1 h. The mixture was poured over ice and 500 mL diethyl ether added. The aqueous layer was acidified to pH=3 and the aqueous layer extracted with 3×50 mL diethyl ether. The combined organics were dried over $MgSO_4$ filtered and dried in vacuo to give 25.3 g (97%) of Intermediate 8 as a white solid.

9.3—Synthesis of 3,5-di-tertbutyl salicyl-N-2,4,6-trimethyl phenyl amino zirconium dimethyl amide (Complex 4)

In the $N_2$ glovebox, a 100 mL schlenk was loaded with 3.72 g (13.9 mmol) $Zr(NMe_2)_4$, 4.92 g (13.9 mmol) Intermediate 8 and 50 mL toluene. The mixture was refluxed for 12 h, filtered and dried in vacuo to yield 3,5-di-tertbutyl salicyl-N-2,4,6-trimethyl phenyl amino zirconium dimethyl amide as a yellow solid.

Example 10

10.1—Synthesis of dilithio 3,5-di-tertbutyl salicyl-N-2,4,6-trimethyl phenyl amine (Intermediate 9)

In a $N_2$ glovebox, a 500 mL schlenk was loaded with 10 g (28 mmol) of Intermediate 8 and covered with 250 mL diethyl ether. At 0° C., 35.3 ml (57 mmol) of a solution of n-Butyl lithium (1.6M in hexanes) was added dropwise. The mixture was warmed to room temperature and stirred for 3 hours. Removal of the volatile components of the reaction mixture gave 10.0 g (98%) of Intermediate 9.

10.2—Synthesis of 3,5-di-tertbutyl salicyl-N-2,4,6-trimethyl phenyl amino hafnium dichloride (Complex 5)

In a nitrogen glovebox, a 100 mL schlenk was loaded with 2.19 g (6.84 mmol) $HfCl_4$ and 2.5 g (6.84 mmol) of Intermediate 9. At −78° C., 50 mL toluene was added dropwise. The mixture was then refluxed for 12 h, filtered, dried in vacuo and extracted into toluene. Filtration followed by removal of the volatile components of the supernatent solution afforded 2.7 g of 3,5-di-tertbutyl salicyl-N-2,4,6-trimethyl phenyl amino hafnium dichoiride as an analytically pure yellow solid.

Polymerisations

Trimethyl aluminum was purchased from Aldrich and used without further purification. MAO was purchased from Aldrich as a 7 wt % solution in toluene and prepared by removing all volatiles in vacuo and washing the residual solid three times with pentane; the final product was dried once more in vacuo and stored in a $N_2$ glovebox.

All air sensitive reagents were handled with standard Schlenk and inert atmosphere glovebox techniques. Toluene and ethylene were purified by passage through activated molecular seives and Q-5 oxygen scavenger (13 wt % Cu on alumina activated by 10% $H_2/N_2$). Diethyl ether and 1-hexene were purified by distillation from a Na°/benzophenone ketyl.

Polymerisation of Ethylene

A 12 oz high-pressure glass bottle equipped with a mechanical stirrer, internal cooling loop and internal pressure and temperature monitors was dried at 50° C. in vacuo for 4 h with frequent flushing with dry $N_2$. In a $N_2$ glovebox, a 10 mL stainless-steel double-ended injection tube was loaded with 5 mL toluene and $2.5 \times 10^{-5}$ mmol Zr/Hf procatalyst and 5 mmol TMA. A second 10 mL stainless-steel double-ended injection tube was loaded with 5 mL toluene and 290 mg (1 mmol) MAO.

Outside the glovebox, the injection tube that was loaded with toluene/MAO was connected to the reactor and its contents injected with a stream of 200 mL toluene under 2 bar $N_2$ back pressure. The reactor was vented, pressurized with 4 bar ethylene and stirred at 1000 rpm at room temperature. After 15 minutes equilibration, Zr/Hf procatalyst and TMA were injected into the reactor under 4 bar ethylene pressure with reactor venting to provide the pressure differential. Using a combination of internal water cooling loops, an ice/water bath and the reaction exotherm, the temperature was maintained at 25° C. for 60 min.

At 30 min, the reaction was quenched by the injection of 10 mL methanol. The reactor was vented and 200 mL methanol was added to precipitate the polymer, which was collected by filtration and dried overnight under reduced pressure.

| | Polymerisation Results | |
|---|---|---|
| Complex | Yield (g of polymer) | Activity (g/mmol.h.b) |
| 4 | 0.78 | 15.6 |
| 5 | 0.76 | 15.2 |
| 3 | 1.37 | 27.4 |

Polymerisation of Propylene

A 12 oz high-pressure glass bottle equipped with a mechanical stirrer, internal cooling loop and internal pressure and temperature monitors was dried at 50° C. in vacuo for 4 h with frequent flushing with dry $N_2$. In a $N_2$ glovebox, a 10 mL stainless-steel double-ended injection tube was loaded with 5 mL toluene and $2.5 \times 10^{-5}$ mmol Zr/Hf procatalyst and 5 mmol TMA. A second 10 mL stainless-steel double-ended injection tube was loaded with 5 mL toluene and 290 mg (1 mmol) MAO.

Outside the glovebox, the injection tube that was loaded with toluene(MAO was connected to the reactor and its contents injected with a stream of 200 mL toluene under 2 bar $N_2$ back pressure. The reactor was vented, pressurized with 4 bar propylene and stirred at 1000 rpm at room temperature. After 15 minutes equilibration, Zr/Hf procatalyst and TMA were injected into the reactor under 4 bar propylene pressure with reactor venting to provide the pressure differential. Using a combination of internal water cooling loops, an ice/water bath and the reaction exotherm, the temperature was maintained at 25° C. for 60 min.

At 30 min, the reaction was quenched by the injection of 10 mL methanol. The reactor was vented and 200 mL methanol was added to precipitate the polymer, which was collected by filtration and dried overnight under reduced pressure.

| | Polymerisation Results | |
|---|---|---|
| Complex | Yield (g of polymer) | Activity (g/mmol.h.b) |
| 4 | 0.66 | 13.2 |
| 5 | 0.41 | 8.2 |
| 3 | 0.53 | 10.6 |

Polymerisation of Ethylene/1-hexene

A 12 oz high-pressure glass bottle equipped with a mechanical stirrer, internal cooling loop and internal pressure and temperature monitors was dried at 50° C. in vacuo for 4 h with frequent flushing with dry $N_2$. In a $N_2$ glovebox, a 10 mL stainless-steel double-ended injection tube was loaded with 5 mL toluene and $2.5 \times 10^{-5}$ mmol Zr/Hf procatalyst and 5 mmol TMA. A second 10 ml stainless-steel double-ended injection tube was loaded with 5 mL toluene and 290 mg (1 mmol) MAO.

Outside the glovebox, the injection tube that was loaded with toluene/MAO was connected to the reactor and its contents injected with a stream of 200 mL toluene under 2 bar $N_2$ back pressure. 30 mL 1-hexene was injected into the reactor under 1.5 bar $N_2$ pressure. The reactor was vented, pressurized with 4 bar ethylene and stirred at 1000 rpm at room temperature. After 15 minutes equilibration, Zr/Hf procatalyst and TMA were injected into the reactor under 4 bar ethylene pressure with reactor venting to provide the pressure differential. Using a combination of internal water cooling loops, an ice/water bath and the reaction exotherm, the temperature was maintained at 25° C. for 60 min.

At 30 min, the reaction was quenched by the injection of 10 mL methanol. The reactor was vented and 200 mL methanol was added to precipitate the polymer, which was collected by filtration and dried overnight under reduced pressure.

| | Polymerisation Results | |
|---|---|---|
| Complex | Yield (g of polymer) | Activity (g/mmol.h.b) |
| 4 | 0.64 | 12.8 |
| 5 | 0.60 | 12.0 |
| 3 | 0.40 | 8.0 |

We claim:

1. Compound comprising the skeletal unit depicted in Formula (I)

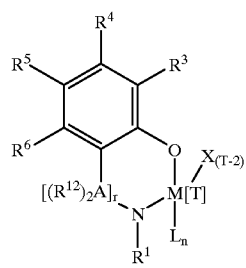

Formula (I)

wherein O is oxygen; N is nitrogen; $R^1$ is hydrogen, hydrocarbyl, substituted hydrocarbyl, heterohydrocarbyl or substituted heterohydrocarbyl; $R^3$, $R^4$, $R^5$ and $R^6$ are hydrogen or hydrocarbyl or heterohydrocarbyl groups containing 1 to 10 carbon atoms and the $R^{12}$ groups are independently selected from hydrogen, hydrocarbyl, substituted hydrocarbyl, heterocarbyl and substituted heterocarbyl; A is carbon or silicon; and r is 1 or more; M is scandium, yttrium, or a Group IV or Group V metal or a lanthanide or actinide; T is the oxidation state of M and is II or greater; X represents a monodentate atom or group covalently or ionically bonded to M; L is a mono- or bidentate molecule datively bound to M, and n is from 0 to 5.

2. Compound according to claim 1 wherein M is a metal from Group IV, or scandium or yttrium.

3. Compound according to claim 1 wherein M is TI(IV), Ti(III), Ti(II), Zr(IV), Zr(III), Zr(II), Hf(IV), Hf(II), Sc(III) or Y(III).

4. Compound according to claim 1 wherein L is an ether, alcohol, amine, ester, phosphine, alkene, alkyne, arene or diene.

5. Compound according to claim 1 wherein n is zero.

6. Compound according to claim 1 wherein the $R^3$, $R^4$, $R^5$ and $R^6$ groups are each independently hydrogen, methyl, ethyl, n-propyl, n-butyl, n-hexyl, or n-octyl, and the $R^{12}$ groups are each independently hydrogen, methyl, ethyl, n-propyl, n-butyl, n-hexyl, n-octyl, methoxy, ethoxy, dimethylamino, phenyl or napththyl.

7. Compound according to claim 1 wherein A is carbon, and/or n is zero, and/or r is from 1 to 5.

8. Compound according to claim 1 wherein $R^1$ is methyl, ethyl, propyl, n-butyl, tertiary-butyl, phenyl, 1-napththyl, 2-napththyl, 2-ethylphenyl, 2,6-diisopropylphenyl, 2,6-di-n-butylphenyl, 2-,6-dimethylphenyl, 2-6-butylphenyl; 2,6-dipheynylphenyl, 2,4,6-trimethylphenyl, 2-6-trifluoromethylphenyl, 4-bromot-2,6-dimethylphenyl, 3,5 dichloro-2,6-diethylphenyl, 2,6,bis(2,6-dimethylphenyl) phenyl, adamantly, triphenylmethyl, 2,6-dimethyl-4-t-butylphenyl, 2,4,6-triphenylphenyl, 2,3,4,5,6,-pentamethylphenyl, or 2-methylenepyridine.

9. Compound according to claim 1 wherein X is selected from $C_1$–$C_{10}$ alkyl, $C_6$–$C_{10}$ aryl, halide, hydride, hydrocarbyloxide, and amide.

10. Compound according to claim 9 wherein X is N,N-dimethylamido, N,N-diethylamido, chloro, bromo, methyl, ethyl, n-propyl, isopropyl, benzyl, n-butyl or n-octyl.

11. Compound comprising the skeletal unit depicted in Formula B

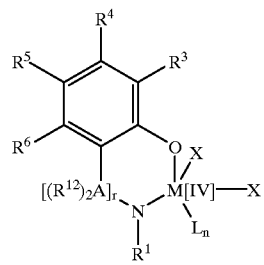

Formula B wherein O is oxygen; N is nitrogen; M is scandium yttrium, or a Group IV or Group V metal or a lanthanide or actinide; L is a mono or bidentate molecule datively bound to M; n is from 0 to 5; $[(R^{12})_2A]_r$ is $CH_2$; each X is $NMe_2$; $R^4$ and $R^6$ are H; $R^3$ and $R^5$ are H or t-Bu; and $R^1$ is t-Bu, 2,6-dimethylphenyl, naphthyl, phenyl or adamantyl; and r is 1 or more.

12. Compound which comprises the skeletal unit as depicted in Formula C or Formula D:

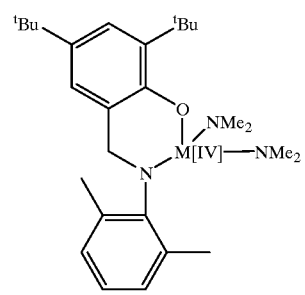

Formula C

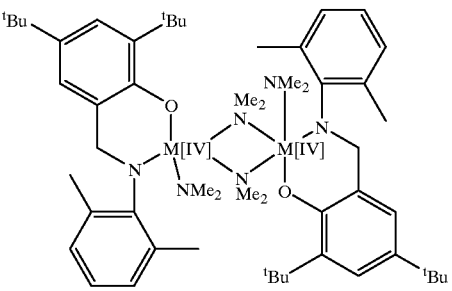

Formula D wherein O is oxygen; N is nitrogen; M is scandium, yttrium or a Group IV or Group V metal or a lanthanide or actinide; L is a mono- or bidentate molecule datively bound to M; and n is from 0 to 5.

* * * * *